United States Patent [19]

Kerb et al.

[11] 4,260,464
[45] Apr. 7, 1981

[54] PROCESS FOR THE PREPARATION OF 17α-(3-IODOBENZOYLOXY)-9α-CHLORO-4-PREGNENE-3,20-DIONES AND THEIR D-HOMO HOMOLOGS

[75] Inventors: Ulrich Kerb; Manfred Stahnke; Rudolf Wiechert, all of Berlin, Fed. Rep. of Germany

[73] Assignee: Schering Aktiengesellschaft, Berlin & Bergkamen, Fed. Rep. of Germany

[21] Appl. No.: 953,323

[22] Filed: Oct. 20, 1978

[30] Foreign Application Priority Data

Oct. 26, 1977 [DE] Fed. Rep. of Germany ....... 2748442

[51] Int. Cl.³ .............................................. B01J 19/08
[52] U.S. Cl. ........................................... 204/158 HA
[58] Field of Search ..................... 204/158 R, 158 HA

[56] References Cited

U.S. PATENT DOCUMENTS

| | | | |
|---|---|---|---|
| 2,681,353 | 6/1954 | Archer | 260/397.4 |
| 3,585,191 | 6/1971 | Mark et al. | 204/158 HA |
| 4,061,661 | 12/1977 | Kerb et al. | 260/397.45 |
| 4,097,678 | 6/1976 | Kerb et al. | 204/158 HA |

OTHER PUBLICATIONS

Breslow et al., JACS 96 (1974), 1973 & 6791.
Snider et al., JACS 97 (1975), 6580.
Breslow et al., JACS 94 (1972), 3276.
Halpern, Chem & Ind. (1962), 1571.

Primary Examiner—Howard S. Williams
Attorney, Agent, or Firm—Millen & White

[57] ABSTRACT

Novel 17α-(3-iodobenzoyloxy)-9α-chloro-4-pregnene-3,20-diones and the D-homo homologs thereof, of the formula

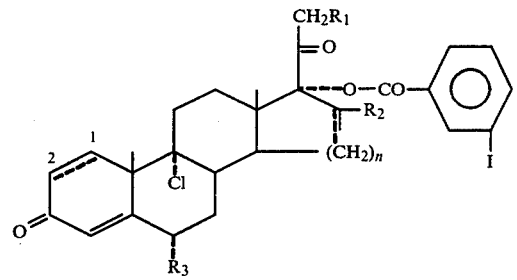

wherein
n is 1 or 2;
$C_1$-----$C_2$ represents a C—C single or C═C double bond;
$R_1$ is hydrogen, hydroxy, or lower acyloxy;
$R_2$ is hydrogen or methyl;
$R_3$ is hydrogen, methyl or fluorine; and
when n is 1, $C_{15}$-----$C_{16}$ represents a C—C single or C═C double bond; and when n is 2, $C_{16}$-----$C_{17}$ represents a C—C single or C═C double bond;

which have valuable pharmacological properties and also serve as intermediates in the preparation of known pharmacologically active compounds, can be prepared by irradiating a 17α-(3-iodobenzoyloxy)-4-pregnene-3,20-dione or a D-homo homolog thereof of the formula

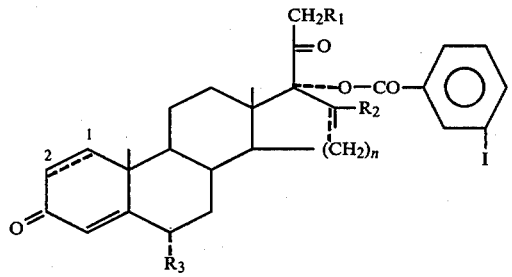

with long wavelength ultraviolet radiation in the presence of phenyliodine dichloride.

8 Claims, No Drawings

PROCESS FOR THE PREPARATION OF 17α-(3-IODOBENZOYLOXY)-9α-CHLORO-4-PREGNENE-3,20-DIONES AND THEIR D-HOMO HOMOLOGS

BACKGROUND OF THE INVENTION

The present invention relates to novel steroid compounds and to a process for the preparation thereof.

SUMMARY OF THE INVENTION

It is an object of this invention to provide new steroid compounds which have antiphlogistic activity and which can be used as intermediates in the preparation of other pharmacologically active compounds, e.g., anti-inflammatory agents.

It is another object of this invention to provide a process for the preparation of these novel compounds which entails selective chlorination of the tertiary C-9 atom of the steroid nucleus in the presence of keto substituents.

Upon further study of the specification and appended claims, further objects and advantages of this invention will become apparent to those skilled in the art.

These objects have been attained by providing 17α-(3-iodobenzoyloxy)-9α-chloro-4-pregnene-3,20-diones and their D-homo homologs of Formula I

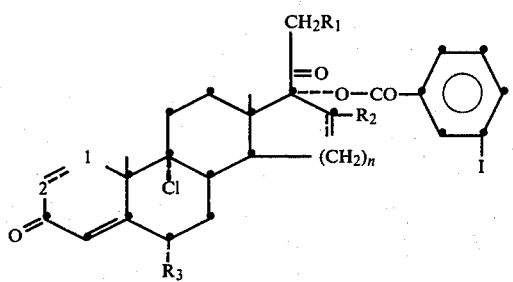

wherein n is 1 or 2;

$C_1$-----$C_2$ represents a C—C single or C═C double bond;

$R_1$ is hydrogen, hydroxy or lower alkanoyloxy or substituted lower akanoyloxy;

$R_2$ is hydrogen or methyl;

$R_3$ is hydrogen, methyl or fluorine; and when n is 1, $C_{15}$-----$C_{16}$ represents a C—C single or C═C double bond; and when n is 2, $C_{16}$-----$C_{17}$ represents a C—C single or C═C double bond.

These objects have further been attained by providing a process for preparing the compounds of Formula I which comprises esterifying a 17α-hydroxy-Δ⁴-3,20-ketopregnene or a D-homo homolog thereof of Formula II

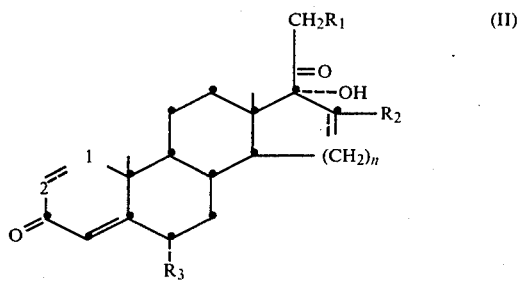

werein $R_1$ is hydrogen or lower akanoyloxy or substituted lower alkanoyloxy;

n, $C_1$-----$C_2$, $R_2$, $R_3$, $C_{15}$-----$C_{16}$ and $C_{16}$-----$C_{17}$ are defined as for Formula I, with m-iodobenzoic acid; and irradiating the resulting 17α-m-iodobenzoyl ester, in the presence of phenyliodine dichloride with long wavelength ultraviolet radiation.

DETAILED DISCUSSION

The compounds of this invention are primarily useful as intermediates for the preparation of pharmacologically valuable compounds. However, they are themselves pharmacologically active, for example, as antiphlogistic agents for mammals including humans.

Lower alkanoyl is understood to mean especially those organic acid residues derived from lower alkanoic acids of up to 4 carbon atoms. Suitable such acid groups include acetyl, propionyl, butyryl, and isobutyryl.

Suitable substituents for the alkanoyl groups include $C_{1-4}$ alkoxy, e.g., methoxy, ethoxy, propoxy and i-butoxy.

The exact structure of the acyloxy residue $R_1$ is not critical. Therefore, there are many contemplated equivalents of the preferred alkanoyl and substituted alkanoyloxy groups. These include methoxyacetyl, ethoxyacetyl, i-butoxyacetyl, ethoxypropionyl and ethoxybutyryl.

When used as antiphlogistic agents, the compounds are generally administered topically in a concentraion of 0.01 to 1% by weight in accordance with the procedure used, e.g., for the administration of the conventional antiphlogistic agent fluocortolone.

Moreover, as antiphlogistic agents, the compounds can be formulated with conventional excipients into medicinal agents in accordance with the conventional methods of galenic pharmacy. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, ointments, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of this invention are dispensed in unit dosage form comprising 1–100 mg in a pharmaceutically acceptable carrier for topical administration.

In one use of the compounds of Formula I as intermediates by saponification of their 17α-(3-iodobenzoyl)-group, $\Delta^4$-3-keto-9α-halo steroids are obtained, for example, in a simple procedure from the compounds of this invention. These end product halo steroids are known as compounds having strong anti-inflammatory effects and minimum undesirable side effects (DAS [German Unpublished Application] No. 1,081,888).

In another use as an intermediate, the corresponding $\Delta^{9(11)}$-unsaturated compounds are obtained by splitting of the 9α-chlorine from the compounds of Formula I. This is accomplished by conventional methods, such as, for example, with silver perchlorate under heating, with alkali or alkaline earth metal carbonates in dimethylformamide or organic bases, such as collidine, lutidine, and pyridine; or with alcoholic potassium hydroxide solution. In the latter method, any ester groups present are likewise cleaved at the same time. The thus-obtained $\Delta^{9(11)}$-unsaturated pregnenes, in turn, constitute a valuable starting material for the production of known 11β-fluoro steroids and 11β-hydroxy steroids, both of which are useful as anti-inflammatory agents.

The 11β-fluoro steroids are obtained, as is known, by chemically adding bromine monofluoride to the $\Delta^{9(11)}$-compound and removing the bromine from the thus-formed 11β-fluoro-9α-bromo compound by reduction with tributyltin hydride (DOS [German Unexamined Laid-Open Application] No. 2,410,443).

The 11β-hydroxy-9α-fluoro steroids are obtained, as is conventional, by chemically adding hypobromous acid to the corresponding $\Delta^{9(11)}$-compound to obtain the 11β-hydroxy-9α-bromo steroid, converting the latter to the 9β,11β-oxido steroid by splitting off hydrogen bromide, and reopening the epoxide ring with hydrogen fluoride (DAS No. 1,026,313).

In order to obtain the 11β-hydroxy steroids, it is also possible to debrominate the 11β-hydroxy-9α-bromo steroid with tribuyltin hydride or with Raney nickel (DAS No. 1,179,549) or with chromium (II) chloride (U.S. Pat. No. 3,026,337).

The intermediates of this invention have the advantage, in particular, that they offer ready access to the 11β-hydroxylated steroids which, as is known, are conventionally prepared by microbiological hydroxylation. Whereas in microbiological process steps, expensive measures must be employed (incubation of the microorganisms, sterility of all working implements, large volumes, etc.), the 11β-hydroxy steroids of this invention are prepared by process steps which can be easily realized technically and industrially. Regarding the operability of the preparative process of this invention, it is most surprising and unexpected that the compounds of Formula I can be prepared in this manner.

It is known from the works of Breslow et al (e.g., J. Amer. Chem. Soc. 96 [1974]: 1973; ibid., 96 [1974]: 6791) that, for steroids esterified in the 3α-position, it is possible to chlorinate the C-5, C-9 and C-14 tertiary carbon atoms with phenyliodine dichloride under the influence of light. Thereafter, hydrogen chloride is split off again, with the formation of a double bond. However, this process has the disadvantage that it is applicable solely to those steroids which do not have any unblocked carbonyl groups, such as in the 3- or 20-position.

In contrast, in accordance with the process of this invention, 9α-chloro-3,20-ketopregnanes are selectively obtained.

It definitely is surprising that the chlorination takes place selectively in the 9-position in accordance with the process of this invention, since it is known, on the one hand, from U.S. Pat. No. 2,681,353 that phenyliodine dichloride in reaction with 20-ketopregnanes, quantitatively results in 21-chloro-20-ketopregnanes. On the other hand, it is known from the works by Halpern (Chem. & Ind. [1962]: 1571) that steroids with double bonds react with phenyliodine dichloride forming the corresponding α-dichloro steroids.

The esterification step of the process of this invention can be suitably conducted by reacting the 17α-hydroxy-$\Delta^4$-3,20-diketopregnene of Formula II with a 3-iodobenzoic acid halogenide, preferably with the chloride or the 3-iodobenzoic acid anhydride, in the presence of a 4-(disubstituted amino)-pyridine, such as 4-dimethylaminopyridine, 4-pyrrolidinopyridine or 4-piperidinopyridine. The reaction is suitably conducted in an appropriate solvent, such as pyridine, lutidine, collidine, benzene, methylene chloride, chloroform, ethylene chloride, ethylene glycol dimethyl ether and the like. This reaction is typically conducted at a temperature of 10°–100° C., in the presence of 1–4 moles of pyridino compound and 1–4 moles of halogenide per moles of pregnene. The concentration of pregnene in the solvent is normally 5–50 wt.%. Typical reaction times are 5 hours to one week. Use of a solvent is optional.

However, it is likewise possible to effect the esterification using a mixed anhydride of 3-iodobenzoic acid, produced in situ by reacting trifluoroacetic anhydride with 3-iodobenzoic acid. This reaction is advantageously carried out in an organic solvent, such as in benzene, anisole, methylene chloride and the like, at temperatues of 10°–100° C. Generally, 1–4 moles of anhydride per mole of pregnene are employed with reaction times of 5 hours to one week. Normally, the concentration of pregnene in the solvent is 5–50 wt.%.

The 17α-(3-iodobenzoyl) steroid ester produced in the first step is photochemically halogenated with phenyliodine dichloride (also termed dichloroiodobenzene, phenyl iodoisodichloride or iodobenzenedichloride) in a suitable solvent.

Suitable solvents include those which are not attacked by the halogenating agent employed, such as halogenated hydrocarbons, for example, methylene chloride, chloroform, trichloroethylene, dichloroethylene and the like; and aromatic hydrocarbons, such as benzene, chlorobenzene and toluene. These solvents can also optionally be used in the form of mixtures with one another. Normally, the concentration of the pregnene in the solvent is 2–40 wt.%. Usually, 1–1.5 moles of phenyliodine dichloride per mole of pregnene are employed. Advantageously, the reaction is conducted with exclusion of oxygen in a protective gas atmosphere. For this purpose, an inert gas, such as nitrogen or argon, can be passed through the reaction solution.

The photochemical halogenation is optionally conducted in the presence of a scavenger for hydrochloric acid such as alkali and earth alkali metal acetates and hydrogencarbonates, like potassium acetate and sodium hydrogencarbonates. Suitable are also molecular sieves, like an A4 molecule sieve. The concentration of such scavenger substance is not critical. Normally, an excess of 5 to 100 moles per mole of steroid are used.

The photochemical reaction is induced by long-wave ultraviolet light, as produced, for example, by commercially available ultraviolet lamps, e.g., from Ultra-Violet Products Inc., U.S.A. Typically, radiation of wavelengths of 300–400 nm is suitable. Radiation times of 1–60 minutes are generally sufficient. For both the photochemical chlorination step and the prior esterification step, it is preferred that the reaction be conducted under a protective gas atmosphere such as argon, nitrogen, etc.

Chlorination of other steroid substrates with phenyliodine dichloride are also known, e.g., see U.S. Pat. No. 4,061,661.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(a) 3.7 g. of 21-acetoxy-17α-hydroxy-4-pregnene-3,20-dione is stirred in 100 ml. of pyridine with 19.5 g. of dimethylaminopyridine and with 11.2 ml. of 3-iodobenzoic acid chloride in an argon atmosphere at a bath temperature of 80° for 22 hours. The pyridine is removed by distillation under vacuum; the residue is stirred with water, taken up in methylene chloride, and the extract is washed in succession with 1 N hydrochloric acid, sodium bicarbonate solution, and water. After drying over sodium sulfate the solvent is removed under vacuum, and the residue is chromatographed on silica gel. By elution with methylene chloride-ethyl acetate, 4.5 g. of 21-acetoxy-17α-(3-iodobenzoyloxy)-4-pregnene-3,20-dione is obtained; m.p. 224°–226° after recrystallization from methanolmethylene chloride.

UV: $\epsilon_{222} = 34,200$.

(b) 2.8 g. of 21-acetoxy-17α-(3-iodobenzoyloxy)-4-pregnene-3,20-dione is dissolved in 250 ml. of methylene chloride and irradiated in a graduated cylinder, while passing argon through the solution and adding 1.8 g. of phenyliodine dichloride, with an ultraviolet radiator (type XX 15C by Ultra-Violet Products Inc., U.S.A.) at a wavelength of 320–400 nm for 15 minutes. The reaction solution is then washed with 2% sodium bisulfite solution, 2% sodium bicarbonate, and water, dried over sodium sulfate, and evaporated under vacuum. Chromatography on silica gel yields 21-acetoxy-9α-chloro-17α-(3-iodobenzoyloxy)-4-pregnene-3,20-dione.

(c) 630 mg. of 21-acetoxy-9α-chloro-17α-(3-iodobenzoyloxy)-4-pregnene-3,20-dione is dissolved in 60 ml. of acetone, combined with a solution of 340 mg. of silver perchlorate in 20 ml. of water, and heated under reflux for 5 hours. Thereafter, the solvent is distilled off under vacuum; the residue is taken up in methylene chloride and washed in succession with sodium chloride solution, sodium bicarbonate solution, and water, dried, and concentrated. After layer chromatography in the system of methylene chloride-ethyl acetate 95:5 and recrystallization from methylene chloride-ethyl acetate, 21-acetoxy-17α-(3-iodobenzoyloxy)-4,9(11)-pregnadiene-3,20-dione is obtained, m.p. 251°–253°.

UV: $\epsilon_{222} = 36,400$.

EXAMPLE 2

(a) 4 g. of 17α-hydroxy-4-pregnene-3,20-dione is dissolved in 55 ml. of dimethylformamide and 7 ml. of triethylamine. The reaction mixture is combined with 3.5 ml. of iodobenzoic acid chloride and 2.9 g. of dimethylaminopyridine and agitated under argon for 20 hours at a bath temperature of 80°. The mixture is then poured into ice water, acidified with 1 N hydrochloric acid, the thus-precipitated product is vacuum-filtered, washed with water, and dissolved in methylene chloride. The methylene chloride solution is evaporated and the residue chromatographed on silica gel. By elution with methylene chloride-ethyl acetate, 17α-(3-iodobenzoyloxy)-4-pregnene-3,20-dione is obtained; m.p. 184°–185° after recrystallization from acetone-hexane.

UV: $\epsilon_{222} = 37,100$.

(b) One gram of 17α-(3-iodobenzoyloxy)-4-pregnene-3,20-dione is dissolved in 100 ml. of methylene chloride, combined with 700 mg. of phenyliodine dichloride and irradiated for 10 minutes with long-wave UV light. The mixture is worked up as described in Example 1(b). After chromatography on silica gel and recrystallization from acetone-hexane, 9α-chloro-17α-3-iodobenzoyloxy-4-pregnene-3,20-dione is obtained; m.p. 213°–214° (decomposition).

(c) 320 mg. of 9α-chloro-17α-m-iodobenzoyloxy-4-pregnene-3,20-dione is dissolved in 30 ml. of acetone, combined with a solution of 140 mg. of silver perchlorate in 10 ml. of water and heated under reflux for 1 hour. After the mixture has been worked up and chromatographed as described in Example 1(c), 17α-m-iodobenzoyloxy-4,9(11)-pregnadiene-3,20-dione is obtained which melts at 188°–189° after recrystallization from acetonehexane.

EXAMPLE 3

333 mg. of 17α-m-iodobenzoyloxy-4,9(11)-pregnadiene-3,20-dione is stirred in 40 ml. of 5% methanolic potassium hydroxide solution under argon for 2 hours at room temperature. After neutralization with acetic acid, the mixture is concentrated under vacuum, taken up in methylene chloride, washed with water, and evaporated. Recrystallization from acetone-hexane yields 210 mg. of 17α-hydroxy-4,9(11)-pregnadiene-3,20-dione, m.p. 212°–213°.

EXAMPLE 4

(a) 2 g. of 21-acetoxy-17α-hydroxy-1,4-pregnadiene-3,20-dione is agitated in 75 ml. of pyridine and 9.75 g. of dimethylaminopyridine and 7 ml. of 3-iodobenzoic acid chloride under argon for 23 hours at a bath temperature of 80°. After the mixture has been worked up and chromatographed as described in Example 1(a), 2.3 g. of 21-acetoxy-17α-(3-iodobenzoyloxy)1,4-pregnadiene-3,20-dione is obtained; m.p. 213.5°–215° after recrystallization from acetone-hexane.

UV: $\epsilon_{222}=38,000$.

(b) 730 mg. of 21-acetoxy-17α-(3-iodobenzoyloxy)-1,4-pregnadiene-3,20-dione is dissolved in 100 ml. of methylene chloride, combined with 430 mg. of phenyliodine dichloride, and irradiated under argon for 7 minutes with long-wave UV light. After the mixture has been worked up as described in Example 1(b) and recrystallized from acetone-hexane, 960 mg. of 9α-chloro-21-acetoxy-17α-(3-iodobenzoyloxy)-1,4-pregnadiene-3,20-dione is obtained; m.p. 231°–232° (decomposition).

UV: $\epsilon_{222}=36,000$.

(c) 200 mg. of 9α-chloro-21-acetoxy-17α-(3-iodobenzoyloxy)-1,4-pregnadiene-3,20-dione is dissolved in 20 ml. of acetone; 250 mg. of silver perchlorate in 6 ml. of water is added thereto, and the mixture is heated under reflux for 16 hours. After the mixture has been worked up and recrystallized from acetone-hexane, 21-acetoxy-17α-(3-iodobenzoyloxy)-1,4,9(11)-pregnatriene-3,20-dione is obtained, m.p. 209°–210°.

UV: $\epsilon_{222}=40,100$.

EXAMPLE 5

(a) 21-Acetoxy-17α-hydroxy-16β-methyl-1,4-pregnadiene-3,20-dione is reacted analogously to Example 1(a) to obtain 21-acetoxy-17α-(3-iodobenzoyloxy)-16β-methyl-1,4-pregnadiene-3,20-dione (m.p. 208°–210°).

(b) 1.2 g. of 21-acetoxy-17α-(3-iodobenzoyloxy)-16β-methyl-1,4-pregnadiene-3,20-dione is combined in 130 ml. of methylene chloride with 800 mg. of phenyliodine dichloride and irradiated under argon for 10 minutes with long-wave UV light. After the reaction mixture has been worked up and crystallized, 1.05 g. of 9α-chloro-21-acetoxy-17α-(3-iodobenzoyloxy)-16β-methyl-1,4-pregnadiene-3,20-dione is obtained; m.p. 238°–240° (decomposition).

(c) 900 mg. of 9α-chloro-21-acetoxy-17α-(3-iodobenzoyloxy)-16β-methyl-1,4-pregnadiene-3,20-dione is dissolved in 100 ml. of acetone, combined with 800 mg. of silver perchlorate in 8 ml. of water, and heated under reflux for 16 hours. After the mixture has been worked up and crystallized from methylene chloride-ethyl acetate, 650 mg. of 21-acetoxy-17α-(3-iodobenzoyloxy)-16β-methyl-1,4,9(11)-pregnatriene-3,20-dione is obtained, m.p. 243°–245°.

EXAMPLE 6

1.5 g. of 9α-chloro-21-acetoxy-17α-(3-iodobenzoyloxy)-1,4-pregnadiene-3,20-dione is heated to boiling under reflux in 100 ml. of 5% methanolic potassium hydroxide solution under argon for 2 hours. The mixture is then neutralized with acetic acid, concentrated under vacuum, and the residue is taken up in methylene chloride, washed with water, and evaporated. Recrystallization from acetone-hexane yields 17α,21-dihydroxy-1,4,9(11)-pregnatriene-3,20-dione, m.p. 224°–226° (decomposition).

EXAMPLE 7

392 mg. of 9α-chloro-21-acetoxy-17α-(3-iodobenzoyloxy)-1,4-pregnadiene-3,20-dione is dissolved in 15 ml. of methanol and 15 ml. of methylene chloride, cooled to 0°, and combined with 1.8 ml. of 2 N sodium hydroxide solution. The solution is agitated under argon for 30 minutes at 0°. Thereafter the mixture is neutralized with acetic acid, evaporated under vacuum, and worked up. After crystallization from acetone, 176 mg. of 9α-chloro-17α,21-dihydroxy-1,4-pregnadiene-3,20-dione is obtained, m.p. 229° (decomposition).

EXAMPLE 8

50 mg. of 9α-chloro-17α,21-dihydroxy-1,4-pregnadiene-3,20-dione is heated under reflux in 10 ml. of acetone, 10 ml. of tetrahydrofuran, and 1 ml. of water with 200 mg. of silver perchlorate for 20 hours. After the mixture has been worked up and crystallized from acetone-hexane, 17α,21-dihydroxy-1,4,9(11)-pregnatriene-3,20-dione is obtained, m.p. 225° (decomposition).

EXAMPLE 9

376 mg. of 21-acetoxy-17α-hydroxy-4-pregnene-3,20-dione is heated for 17 hours under reflux in 10 ml. of methylene chloride with 5 g. of dimethylaminopyridine and 0.56 ml. of 3-iodobenzoic acid chloride. The mixture is then diluted with methylene chloride and washed in succession with dilute hydrochloric acid, sodium bicarbonate solution and water. After removal of the solvent and chromatography on silica gel, 530 mg. of 21-acetoxy-17α-(3-iodobenzoyloxy)-4-pregnene-3,20-dione is obtained, m.p. 224.5°–226°.

EXAMPLE 10

Analogously to Examples 1(a) and 1(b), 21-acetoxy-6α-fluoro-17α-hydroxy-4-pregnene-3,20-dione yields 9α-chloro-21-acetoxy-6α-fluoro-17α-(3-iodobenzoyloxy)-4-pregnene-3,20-dione, m.p. 243° (decomposition).

EXAMPLE 11

By alkaline hydrolysis, 6α-methyl-17α,21-dihydroxy-4,9(11)-pregnadiene-3,20-dione (m.p. 171°–173°) and 6α-fluoro-17α,21-dihydroxy-4,9(11)-pregnadiene-3,20-dione (m.p. 217°–219°, decomposition) are obtained from 9α-chloro-21-acetoxy-17α-(3-iodobenzoyloxy)-6α-methyl-4-pregnene-3,20-dione and 9α-chloro-6α-fluoro-21-acetoxy-17α-(3-iodobenzoyloxy)-4-pregnene-3,20-dione.

EXAMPLE 12

(a) 1.61 g. of 21-acetoxy-17α-hydroxy-6α-methyl-4 pregnene-3,20-dione is agitated for 5 days in 10 ml. of methylene chloride with 1.96 g. of dimethylaminopyridine and 3.82 g. of 3-iodobenzoic acid anhydride at room temperature. After the mixture has been worked up and chromatographed on silica gel, 2.18 g. of 21-acetoxy-17α-(3-iodobenzoyloxy)-6α-methyl-4-pregnene-3,20-dione is obtained, m.p. 217°–218° (acetone-hexane).

(b) 632.5 mg. of 21-acetoxy-17α-(3-iodobenzoyloxy)-6α-methyl-4-pregnene-3,20-dione is irradiated in 50 ml. of methylene chloride, after adding 1 g. of potassium acetate and 330 mg. of phenyl iododichloride, with UV light for 5 minutes. After the mixture has been worked up and chromatographed, 570 mg. of 9α-chloro-21-acetoxy-17α-(3-iodobenzoyloxy)-6α-methyl-4-pregnene-3,20-dione is produced, m.p. 248°–251°, decomposition (acetone).

(c) 333.5 mg. of 9α-chloro-21-acetoxy-17α-(3-iodobenzoyloxy)-6α-methyl-4-pregnene-3,20-dione is heated in 5 ml. of acetic acid with 170 mg. of silver nitrate for 15 minutes to 100°. The mixture is precipitated in ice-cold sodium chloride solution, vacuum-filtered, and the product extracted with methylene chloride. Recrystallization from acetone yields 230 mg. of 21-acetoxy-17α-(3-iodobenzoyloxy)-6α-methylpregna-4,9(11)-diene-3,20-dione, m.p. 246°–248°.

EXAMPLE 13

(a) 9.4 g. of 21-acetoxy-17α-hydroxy-1,4-pregnadiene-3,20-dione is agitated in 250 ml. of methylene chloride with 24.45 g. of dimethylaminopyridine and 47.8 g. of 3-iodobenzoic acid anhydride for 84 hours at room temperature. The mixture is chromatographed on silica gel without being worked up. With toluene/ether, 21-acetoxy-17α-(3-iodobenzoyloxy)-1,4-pregnadiene-3,20-dione is eluted and recrystallized from acetone-hexane; m.p. 213.5°–215°. Yield: 72.5% of theory.

(b) Reactants:
- 4.932 g. of 21-acetoxy-17α-(3-iodobenzoyloxy)-1,4-pregnadiene-3,20-dione
- 500 ml. of freshly distilled methylene chloride
- 16 g. of potassium acetate, pulverized and dried over phosphorus pentoxide under vacuum
- 2.75 g. of iodobenzene dichloride (washed with $CCl_4$ and pentane)

In a graduated cylinder with magnetic agitator, capacity 500 ml., methylene chloride and potassium acetate are stirred for 20 minutes while introducing argon into the reaction mixture. Then, phenyl iododichloride is added, the mixture is agitated for 5 minutes, and then the iodobenzoate is added. The mixture is irradiated with a UV radiator of the type XX 15 C for 5 minutes. Since a trace of starting material is still present, as determined by thin-layer chromatography, 250 mg. of phenyl iododichloride is added and the mixture irradiated once again for 10 minutes.

The solution is washed with respectively 250 ml. of 5% sodium bisulfite solution, 250 ml. of 5% sodium bicarbonate solution, and water, dried, and evaporated. The residue (5.86 g.) is triturated with pentane. The crystallized product (5.3 g.) is utilized directly in the hydrogen chloride splitting off reaction, thus obtaining 21-acetoxy-9α-chloro-17α-(3-iodobenzoyloxy)-1,4-pregnadiene-3,20-dione, m.p. 231°–232° (decomposition).

With a parallel batch of the same dimension, irradiation was carried out in a graduated cylinder having a capacity of 1,000 ml. and a diameter of 85 mm., using an immersion lamp Hanau TQ 150 by Quarzlampen GmbH, Hanau.

Yield and quality of the thus-obtained products were identical.

EXAMPLE 14

5.36 g. of 21-acetoxy-9α-chloro-17α-(3-iodobenzoyloxy)-1,4-pregnadiene-3,20-dione is dissolved in 80 ml. of glacial acetic acid at 100°; 2.8 g. of silver nitrate is added to the reaction mixture and the latter is stirred for 45 minutes at a bath temperature of 100°. After cooling to room temperature, 1.7 g. of potassium acetate is added, and the acetic acid is removed by distillation on a forced circulation evaporator. The residue is taken up in methylene chloride, washed with NaCl solution, and the silver chloride is suctioned off via a G4 porous filter plate. The filtrate is washed with sodium bicarbonate solution and water, dried, and evaporated under vacuum. The residue (5.19 g.) is chromatographed on silica gel. Elution is carried out with 1.5 l. of methylene chloride/1.5 l. of methylene chloride/ethyl acetate 1:1. After crystallization from ethyl acetate, 3.76 g. of 21-acetoxy-17α-(3-iodobenzoyloxy)-1,4,9(11)-pregnatriene-3,20-dione is obtained, m.p. 209°–210°.

EXAMPLE 15

(a) 18.82 g. of 21-acetoxy-17α-hydroxy-4-pregnene-3,20-dione is stirred in 100 ml. of methylene chloride with 24.45 g. of dimethylaminopyridine and 47.8 g. of 3-iodobenzoic acid anhydride at room temperature. The mixture is completely dissolved after 5 hours, and the reaction is finished after 64 hours.

To work up the reaction mixture, the latter is diluted with 2 l. of methylene chloride and washed in succession with 500 ml. of water, 500 ml. of normal hydrochloric acid, 500 ml. of water, twice with respectively 500 ml. of 5% sodium bicarbonate solution, and once again with 500 ml. of water.

After drying over sodium sulfate and evaporation under vacuum, 33.9 g. of crude 21-acetoxy-17α-(3-iodobenzoyloxy)-4-pregnene-3,20-dione is obtained. Recrystallization from acetone yields 26.90 g. of iodobenzoate; m.p. 224°–226°.

By chromatography, additional iodobenzoate can be isolated from the mother liquors.

(b) 4.95 g. of 21-acetoxy-17α-(3-iodobenzoyloxy)-4-pregnene-3,20-dione is irradiated in 500 ml. of methylene chloride after adding 10 g. of potassium acetate and 3.3 g. of phenyl iododichloride, using an immersion lamp Hanau TQ 150, for 5 minutes. The mixture is then worked up, thus obtaining 4.9 g. of 9α-chloro-21-acetoxy-17α-(3-iodobenzoyloxy)-4-pregnene-3,20-dione, m.p. 256°–259° (decomposition).

EXAMPLE 16

(a) 4.7 g. of 21-acetoxy-17aα-hydroxy-D-homo-4-pregnene-3,20-dione is heated under reflux in 600 ml. of methylene chloride with 11.7 g. of dimethylaminopyridine and 6.7 ml. of 3-iodobenzoic acid chloride for 22 hours. The reaction mixture is worked up by dilution with methylene chloride, filtration, washing of the filtrate with dilute hydrochloric acid, sodium bicarbonate solution, and water, drying over sodium sulfate, and evaporation. The residue is chromatographed on silica gel. Elution with methylene chloride/ethyl acetate yields 21-acetoxy-17aα-(3-iodobenzoyloxy)-D-homo-4-pregnene-3,20-dione, m.p. 187°–188°.

UV: $\epsilon_{221} = 36,000$.

(b) 1.9 g. of 21-acetoxy-17aα-(3-iodobenzoyloxy)-D-homo-4-pregnene-3,20-dione is dissolved in 150 ml. of methylene chloride and irradiated for 7 minutes in a graduated cylinder while passing argon through the reaction mixture and while adding 0.92 g. of iodobenzene dichloride with the use of an ultraviolet radiator (type XX 15C by Ultra-Violet Products Inc., U.S.A.; 320–400 nm.). The reaction solution is then washed with 2% sodium sulfite solution, 2% sodium bicarbonate solution, and water, dried over sodium sulfate, and evaporated under vacuum. After chromatography and crystallization from ethyl acetate, 21-acetoxy-9α-chloro-17aα-(3-iodobenzoyloxy)-D-homo-4-pregnene-3,20-dione is obtained, m.p. 204°–205° (decomposition).

UV: $\epsilon_{222} = 35,200$ (methanol).

EXAMPLE 17

200 mg. of 21-acetoxy-9α-chloro-17aα-(3-iodobenzoyloxy)-D-homo-4-pregnene-3,20-dione is heated under reflux in 20 ml. of acetone and 6 ml. of water with 500 mg. of silver perchlorate for one hour. Subsequently the solvent is removed under vacuum, the residue is taken up in methylene chloride, washed in succession with sodium chloride solution and water, dried, and concentrated. The residue is recrystallized from acetone/hexane, thus obtaining 21-acetoxy-17aα-(3-iodobenzoyloxy)-D-homo-4,9(11)-pregnadiene-3,20-dione, m.p. 191.5°–194°.

EXAMPLE 18

(a) Under argon gas, 2.6 g. of 17aα-hydroxy-D-homo-1,4-pregnadiene-3,20-dione is agitated at a bath temperature of 90° for 24 hours in 100 ml. of pyridine with 8.2 g. of dimethylaminopyridine and 9.2 ml. of 3-iodobenzoic acid chloride. The pyridine is then removed under vacuum by distillation, the residue is combined under agitation with water, and then extracted with methylene chloride. The extract is washed with dilute hydrochloric acid, sodium bicarbonate solution, and water, dried over sodium sulfate, the solvent is removed under vacuum, and the residue is chromatographed on silica gel. Recrystallization from acetone/hexane yields 17aα-(3-iodobenzoyloxy)-D-homo-1,4-pregnadiene-3,20-dione, m.p. 223°–225°.

(b) 1.4 g. of 17aα-(3-iodobenzoyloxy)-D-homo-1,4-pregnadiene-3,20-dione is dissolved in 120 ml. of methylene chloride, and then 0.75 g. of iodobenzene dichloride is added to the reaction mixture and the latter is irradiated with long-wave ultraviolet light. The mixture is worked up as described in Example 16. Chromatography and crystallization from acetone/hexane yields 9α-chloro-17aα-(3-iodobenzoyloxy)-D-homo-1,4-pregnadiene-3,20-dione, m.p. 233° (decomposition).

EXAMPLE 19

Under argon, 300 mg. of 9α-chloro-17aα-(3-iodobenzoyloxy)-D-homo-1,4-pregnadiene-3,20-dione is heated under reflux in 20 ml. of 5% methanolic potassium hydroxide solution for 2 hours. The mixture is then neutralized with acetic acid, concentrated under vacuum, and the residue is chromatographed on silica gel. Recrystallization from acetone/hexane yields 17aα-hydroxy-D-homopregna-1,4,9(11)-triene-3,20-dione, m.p. 190°–191°.

UV: $\epsilon_{239} = 15,600$.

EXAMPLE 20

(a) 1.4 g. of 17aα-hydroxy-D-bromo-4-pregnene-3,20-dione is stirred in 50 ml. of pyridine with 1.4 ml. of 3-iodobenzoic acid chloride and 12.5 g. of dimethylaminopyridine for 21 hours at 80° under argon gas. After the mixture has been worked up as described in Example 18 and then chromatographed on silica gel, amorphous 17aα-(3-iodobenzoyloxy)-D-homo-4-pregnene-3,20-dione is obtained.

UV: $\epsilon_{222} = 35,600$.

(b) 172.3 mg. of 17aα-(3-iodobenzoyloxy)-D-homo-4-pregnene-3,20-dione is dissolved in 30 ml. of methylene chloride, combined with 91.2 mg. of iodobenzene dichloride, and irradiated for 3 minutes with long-wave ultraviolet light. Thereafter another 91.2 mg. of iodobenzene dichloride is added, and the mixture is irradiated for another 3 minutes. After the mixture has been worked up as described in Example 16 and subjected to layer chromatography, recrystallization from acetone/hexane yields 9α-chloro-17aα-(3-iodobenzoyloxy)-D-homo-4-pregnene-3,20-dione, melting at 210° under decomposition.

EXAMPLE 21

100 mg. of 9α-chloro-17aα-(3-iodobenzoyloxy)-D-homo-4-pregnene-3,20-dione is heated to boiling for 1 hour in 12 ml. of acetone and 2 ml. of water with 200 mg. of silver perchlorate. After the mixture has been worked up as described in Example 17 and recrystallized, 17aα-(3-iodobenzoyloxy)-D-homopregna-4,9(11)-diene-3,20-dione is obtained, m.p. 261°–263°.

UV: $\epsilon_{222} = 35,900$.

EXAMPLE 22

Analogously to Examples 16(a) and 16(b),
21-acetoxy-6α-methyl-17aα-hydroxy-D-homo-4-pregnene-3,20-dione and
21-acetoxy-6α-methyl-17aα-hydroxy-D-homo-1,4-pregnadiene-3,20-dione
are reacted to yield
9α-chloro-21-acetoxy-6α-methyl-17aα-(3-iodobenzoyloxy)-D-homo-4-pregnene-3,20-dione, m.p. 198° (decomposition) and
9α-chloro-21-acetoxy-6α-methyl-17aα-(3-iodobenzoyloxy)-D-homopregna-1,4-diene-3,20-dione, m.p. 209° (decomposition).

EXAMPLE 23

Analogously to Example 17,
9α-chloro-21-acetoxy-6α-methyl-17aα-(3-iodobenzoyloxy)-D-homo-4-pregnene-3,20-dione and
9α-chloro-21-acetoxy-6α-methyl-17aα-(3-iodobenzoyloxy)-D-homopregna-1,4-diene-3,20-dione
yield
21-acetoxy-6α-methyl-17aα-(3-iodobenzoyloxy)-D-homopregna-4,9(11)-diene-3,20-dione, m.p. 213°–215°, and
21-acetoxy-6α-methyl-17aα-(3-iodobenzoyloxy)-D-homopregna-1,4,9(11)-triene-3,20-dione, m.p. 229°–231°.

EXAMPLE 24

(a) 7.5 g. of 17aα-hydroxy-D-homopregna-4,16-diene-3,20-dione is agitated at room temperature for 47 hours in 20 ml. of methylene chloride with 5.4 g. of dimethylaminopyridine and 10.5 g. of 3-iodobenzoic acid anhydride. After the mixture has been worked up, chromatographed on silica gel, and recrystallized from acetone, 10.1 g. of 17aα-(3-iodobenzoyloxy)-D-homopregna-4,16-diene-3,20-dione is obtained, m.p. 211°–212°.

(b) A graduated cylinder is charged with 1,950 ml. of methylene chloride, 33 g. of potassium acetate, and 5.05 g. of phenyl iododichloride. Argon is introduced into the reaction mixture. After adding 9.5 g. of 17aα-(3-iodobenzoyloxy)-D-homopregna-4,16-diene-3,20-dione, the mixture is irradiated with long-wave ultraviolet light for 15 minutes. In order to work up the reaction mixture, the latter is washed with 5% sodium bisulfite solution, 5% sodium bicarbonate solution, and water. The methylene chloride solution is dried over sodium sulfate and evaporated under vacuum. The residue is triturated with hexane and recrystallized from acetone, thus obtaining 9.65 g. of 9α-chloro-17aα-(3-iodobenzoyloxy)-D-homopregna-4,16-diene-3,20-dione, m.p. 212°–215° (decomposition).

(c) 6.68 g. of 9α-chloro-17aα-(3-iodobenzoyloxy)-D-homopregna-4,16-diene-3,20-dione is dissolved in 250 ml. of tetrahydrofuran. Then, 4.96 g. of silver perchlorate monohydrate, dissolved in 75 ml. of water, is added to the reaction mixture, and the latter is heated under reflux for 7 hours. For working up purposes, 10 ml. of pyridine is added and the tetrahydrofuran is distilled off under vacuum. The residue is shaken with methylene chloride and sodium chloride solution, the silver salts are removed by filtration, the methylene chloride phase is separated, washed, and evaporated. Chromatography and recrystallization from acetone yield 4.85 g. of 17aα-(3-iodobenzoyloxy)-D-homopregna-4,9(11),16-triene-3,20-dione, m.p. 217°–218°.

EXAMPLE 25

(a) 420 mg. of 21-acetoxy-6α-fluoro-17aα-hydroxy-D-homo-4-pregnene-3,20-dione is agitated in 5 ml. of methylene chloride with 978 mg. of dimethylaminopyridine and 1.91 g. of 3-iodobenzoic acid anhydride for 7 days at room temperature. After chromatography on silica gel and recrystallization from acetone/hexane, 438 mg. of 21-acetoxy-6α-fluoro-17aα-(3-iodobenzoyloxy)-D-homo-4-pregnene-3,20-dione is obtained, m.p. 228°–229°.

(b) A graduated cylinder is charged with 76 ml. of methylene chloride, 1.26 g. of potassium acetate, and 192 mg. of phenyl iododichloride. Argon is introduced, 410 mg. of 21-acetoxy-6α-fluoro-17aα-(3-iodobenzoyloxy)-D-homo-4-pregnene-3,20-dione is added to the reaction mixture, and the latter is irradiated for 5 minutes with an ultraviolet radiator. After the mixture has been worked up and the crude product has been triturated with pentane and recrystallized from acetone, 418 mg. of 9α-chloro-21-acetoxy-6α-fluoro-17aα-(3-iodobenzoyloxy)-D-homo-4-pregnene-3,20-dione is obtained, m.p. 233°–234° (decomposition).

(c) 90.2 mg. of silver perchlorate monohydrate is dissolved in 5 ml. of pyridine, concentrated under vacuum, and then a solution of 137 mg. of 9α-chloro-21-acetoxy-6α-fluoro-17aα-(3-iodobenzoyloxy)-D-homo-4-pregnene-3,20-dione in 10 ml. of glacial acetic acid is added, and the mixture is heated for 90 minutes to 100°. After the mixture has been worked up and crystallized from acetone/hexane, 114 mg. of 21-acetoxy-6α-fluoro-17aα-(3-iodobenzoyloxy)-D-homopregna-4,9(11)-diene-3,20-dione is obtained, m.p. 225°–226° (decomposition).

EXAMPLE 26

(a) At room temperature, 433 mg. of 21-ethoxyacetyloxy-17aα-hydroxy-D-homo-4-pregnene-3,20-dione is agitated for 7 days in 5 ml. of methylene chloride with 978 mg. of dimethylaminopyridine and 1.91 g. of 3-iodobenzoic acid anhydride. The mixture is worked up, chromatographed on silica gel, and recrystallized from isopropyl ether, thus obtaining 21-ethoxyacetyloxy-17aα-(3-iodobenzoyloxy)-D-homo-4-pregnene-3,20-dione, m.p. 169°–171°.

(b) Analogously to Example 24, 400 mg. of 21-ethoxyacetyloxy-17aα-(3-iodobenzoyloxy)-D-homo-4-pregnene-3,20-dione is photochlorinated and worked up, thus obtaining 380 mg. of 9α-chloro-21-ethoxyacetyloxy-17aα-(3-iodobenzoyloxy)-D-homo-4-pregnene-3,20-dione, m.p. 183°–185° (decomposition).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of a 17α-(3-iodobenzoyloxy)-9α-chloro-4-pregnene-3,20-dione of the formula

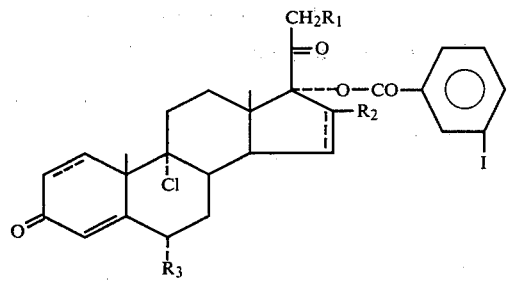

wherein

═══ in all instances represents a C—C single or C═C double bond;

$R_1$ is hydrogen, hydroxy, lower alkanoyloxy or substituted lower alkanoyloxy;

$R_2$ is hydrogen or methyl; and $R_3$ is hydrogen, methyl or fluorine, which comprises irradiating a 17α-(3-iodobenzoyloxy)-4-pregnene-3,20-dione of the formula

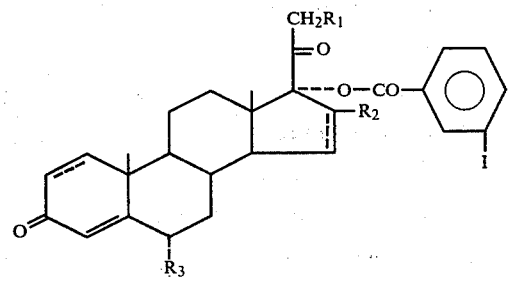

with long wavelength untraviolet radiation in the presence of phenyliodine dichloride.

2. The process of claim 1 which further comprises producing the 17α-(3-iodobenzoyloxy)-4-pregnene-3,20-dione by esterifying a 17α-hydroxy-4-pregnene-3,20-dione of the formula

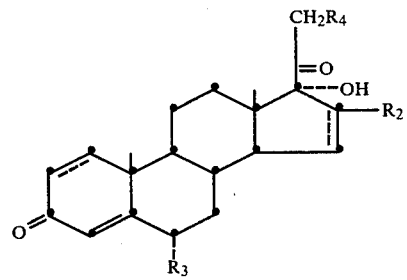

wherein $R_2$ is hydrogen or methyl;

$R_3$ is hydrogen, methyl or fluorine; and $R_4$ is hydrogen, lower alkanoyloxy or substituted lower alkanoyloxy;

with m-iodobenzoic acid.

3. The process of claim 1, wherein the wavelength of the UV radiation is 300-400 nm and the irradiation is conducted for 1-60 minutes under an argon atmosphere.

4. The process of claim 1, wherein the reaction is conducted in the presence of a basic buffer.

5. A process for the preparation of a 17aα-(3-iodobenzoyloxy)-9α-chloro-D-homo-4-pregnene-3,20-dione of the formula

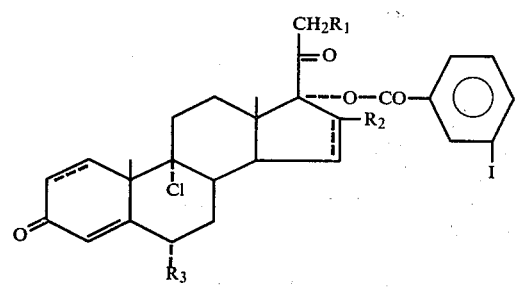

wherein

---- in all instances represents a C—C single or C=C double bond;

$R_1$ is hydrogen, hydroxy, lower alkanoyloxy or substituted lower alkanoyloxy;

$R_2$ is hydrogen or methyl; and $R_3$ is hydrogen, methyl or fluorine, which comprises irradiation a 17aα-(3-iodobenzoyloxy)-D-homo-4-pregnene-3,20-dione of the formula

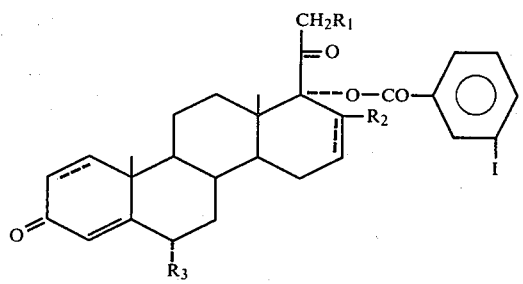

with long wavelength ultraviolet radiation in the presence of phenyliodine dichloride.

6. The process of claim 5 which further comprises producing the 17aα-(3-iodobenzoyloxy)-D-homo-4-pregnene-3,20-dione by esterifying a 17aα-hydroxy-D-homo-4-pregnene-3,20-dione of the formula

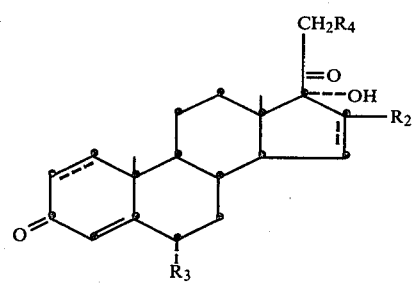

wherein $R_2$ is hydrogen or methyl;

$R_3$ is hydrogen, methyl or fluorine; and $R_4$ is hydrogen, lower alkanoyloxy or substituted lower alkanoyloxy;

with m-iodobenzoic acid.

7. The process of claim 5, wherein the wavelength of the UV radiation is 300-400 nm and the irradiation is conducted for 1-60 minutes under an argon atmosphere.

8. The process of claim 5, wherein the reaction is conducted in the presence of a basic buffer.

* * * * *

UNITED STATES PATENT AND TRADEMARK OFFICE
CERTIFICATE OF CORRECTION

PATENT NO. : 4,260,464

DATED : April 7, 1981

INVENTOR(S) : Kerb et al.

It is certified that error appears in the above—identified patent and that said Letters Patent is hereby corrected as shown below:

Column 15, Claim 5, formula reads:

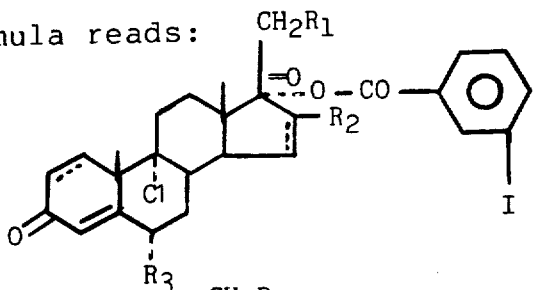

formula should read:

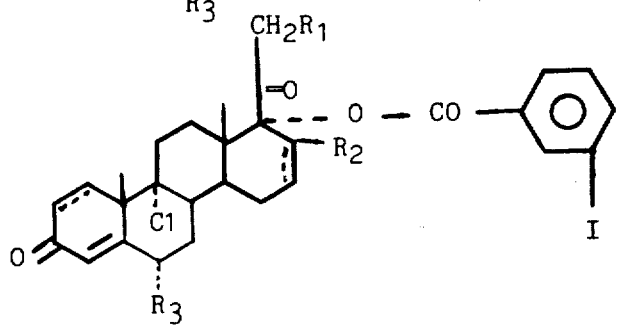

Column 15, Claim 5, line 32 reads: ---- in all instances represents a C-C single or C=C
    should read: ---- in all instances represents a C-C single or C=C Column 15, Claim 5, line 41 reads: which comprises irradiation a 17aα-(3-iodoben-
    should read: which comprises irradiating a 17aα-(3-iodoben-

UNITED STATES PATENT AND TRADEMARK OFFICE
CERTIFICATE OF CORRECTION

PATENT NO. : 4,260,464

DATED : April 7, 1981

INVENTOR(S) : Kerb et al.

It is certified that error appears in the above—identified patent and that said Letters Patent is hereby corrected as shown below:

Column 16, Claim 6, formula reads:

formula should read:

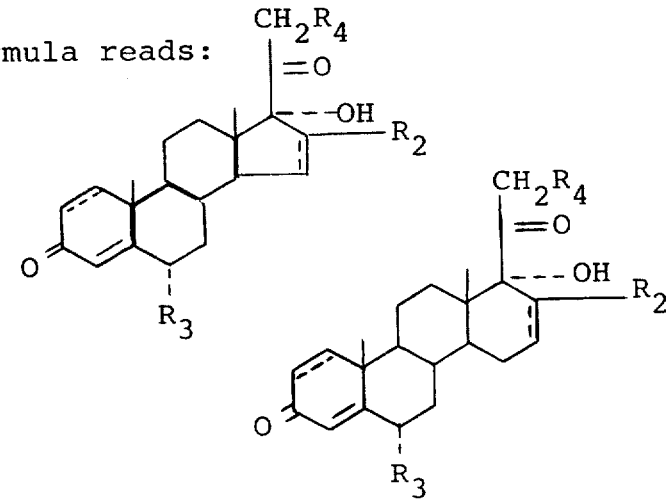

Signed and Sealed this

Fifteenth Day of September 1981

[SEAL]

Attest:

*Attesting Officer*

GERALD J. MOSSINGHOFF

*Commissioner of Patents and Trademarks*